United States Patent
Ko (10) Patent No.: US 6,973,932 B2
(45) Date of Patent: Dec. 13, 2005

(54) TOOTHPICK AND INTERDENTAL BRUSH COMBINATION

(76) Inventor: Wei-Chu Ko, c/o Percy International Patent Corp. P.O. Box 1-79, Taipei (TW)

( * ) Notice: Subject to any disclaimer, the term of this patent is extended or adjusted under 35 U.S.C. 154(b) by 282 days.

(21) Appl. No.: 10/251,959

(22) Filed: Sep. 23, 2002

(65) Prior Publication Data

US 2004/0055619 A1 Mar. 25, 2004

(51) Int. Cl.[7] .......................... A45D 44/18; A46B 9/04; A47L 13/42
(52) U.S. Cl. ........................... 132/309; 15/184; 15/105
(58) Field of Search ................................ 132/328, 309, 132/311, 321, 308, 310; 401/30, 32, 29; 15/106, 15/110, 184, 105, 111, 167.1

(56) References Cited

U.S. PATENT DOCUMENTS

| | | | | |
|---|---|---|---|---|
| 1,679,382 A | * | 8/1928 | Sjobring | 401/82 |
| 2,637,868 A | * | 5/1953 | Hamilton | 401/19 |
| 2,701,378 A | * | 2/1955 | Dugan et al. | 15/111 |
| 4,116,570 A | * | 9/1978 | Parenti | 401/155 |
| 4,266,881 A | * | 5/1981 | Rubens | 401/32 |
| 4,622,984 A | * | 11/1986 | Gaebel | 132/308 |
| 5,046,212 A | * | 9/1991 | O'Conke | 15/105 |
| 6,290,413 B1 | * | 9/2001 | Wang | 401/30 |
| 2001/0054211 A1 | * | 12/2001 | Cabedo-Deslierres et al. | 15/106 |

* cited by examiner

Primary Examiner—Todd E. Manahan
Assistant Examiner—Robyn Doan
(74) Attorney, Agent, or Firm—Troxell Law Office, PLLC (57) ABSTRACT

A toothpick and interdental brush combination comprises a case comprising a lengthwise groove on a side, first and second end openings both in communication with the groove; and an assembly slidable in the case, the assembly comprising a projected trigger member, a first body member extended from the trigger member toward the first end, an interdental brush integrally formed with the first body member at first end, a second body member extended from the trigger member toward the second end, and a toothpick integrally formed with the second body member at the second end. In a storage state both the toothpick and the interdental brush are concealed in the case, or in a use state of the interdental brush or the toothpick a pushing of the trigger member toward the first or the second end causes the interdental brush or the toothpick to project from the first or the second opening respectively.

3 Claims, 16 Drawing Sheets

TOOTHPICK AND INTERDENTAL BRUSH COMBINATION

BACKGROUND OF THE INVENTION

1. Field of the Invention

The present invention relates to dental health equipment and more particularly to an improved toothpick and interdental brush combination which may function as either a toothpick or an interdental brush as desired.

2. Description of Related Art

Conventionally, a toothpick or an interdental brush is used for dislodging food articles from between the teeth. Further, in most cases toothpicks are provided at home or restaurant, i.e., not at many other places. As for toothpicks provided at restaurant, they may be not hygienic because many people have touched them. Furthermore, typically toothpicks are made of wood. There are sufficient reasons to believe that such toothpicks may be contaminated during the manufacturing process.

As for interdental brushes, they are typically used for dislodging larger food articles from between the teeth. As such, many elder persons like to use interdental brushes. Typically, an interdental brush is comprised of a slender stainless steel bar with brushes fastened on one end. Also, the interdental brush is susceptible of bend or even breakage in cleaning the teeth due to its nonrigidness. Thus, it is preferred to use a toothpick for preliminary cleaning prior to using an interdental brush to do the further cleaning. However, toothpick and interdental brush may be located in different places at home. Hence, it is difficult to find them at one time. Moreover, a toothpick is shaped differently from an interdental brush. Hence, it is difficult to place both in a suitable place for ease of accessing. In view of above, there are some problems experienced in the prior art. Thus, continuing improvements in this field are constantly being sought.

SUMMARY OF THE INVENTION

It is an object of the present invention to provide a toothpick and interdental brush combination which can be carried easily for facilitating a cleaning of teeth if such need arises.

It is another object of the present invention to provide a compact toothpick and interdental brush combination for facilitating a cleaning of teeth in any time and/or any place.

It is still another object of the present invention to provide a toothpick and interdental brush combination in which the toothpick and interdental brush sections are located at two opposite ends so that it may function as either a toothpick or an interdental brush as desired.

It is a further object of the present invention to provide a toothpick and interdental brush combination in which both toothpick and interdental brush sections are enclosed by a case structure so as to be hygienic.

To achieve the above and other objects, the present invention provides a toothpick and interdental brush combination comprising an elongate substantially parallelepiped case comprising a lengthwise groove on a side, a first opening at one end, and a second opening at the other end both in communication with the groove; and an elongate toothpick and interdental brush assembly slidable in the case, the toothpick and interdental brush assembly comprising a projected trigger member, a first body member extended from the trigger member toward one end, an interdental brush integrally formed with the first body member at one end, a second body member extended from the trigger member toward the other end, and a toothpick integrally formed with the second body member at the other end; wherein in a storage state both the toothpick and the interdental brush are concealed in the case, or in a use state of the interdental brush or the toothpick a pushing of the trigger member toward one end or the other end causes the interdental brush or the toothpick to project from the first or the second opening respectively.

The above and other objects, features and advantages of the present invention will become apparent from the following detailed description taken with the accompanying drawings.

DETAILED DESCRIPTION OF THE PREFERRED EMBODIMENTS

Figure 1:
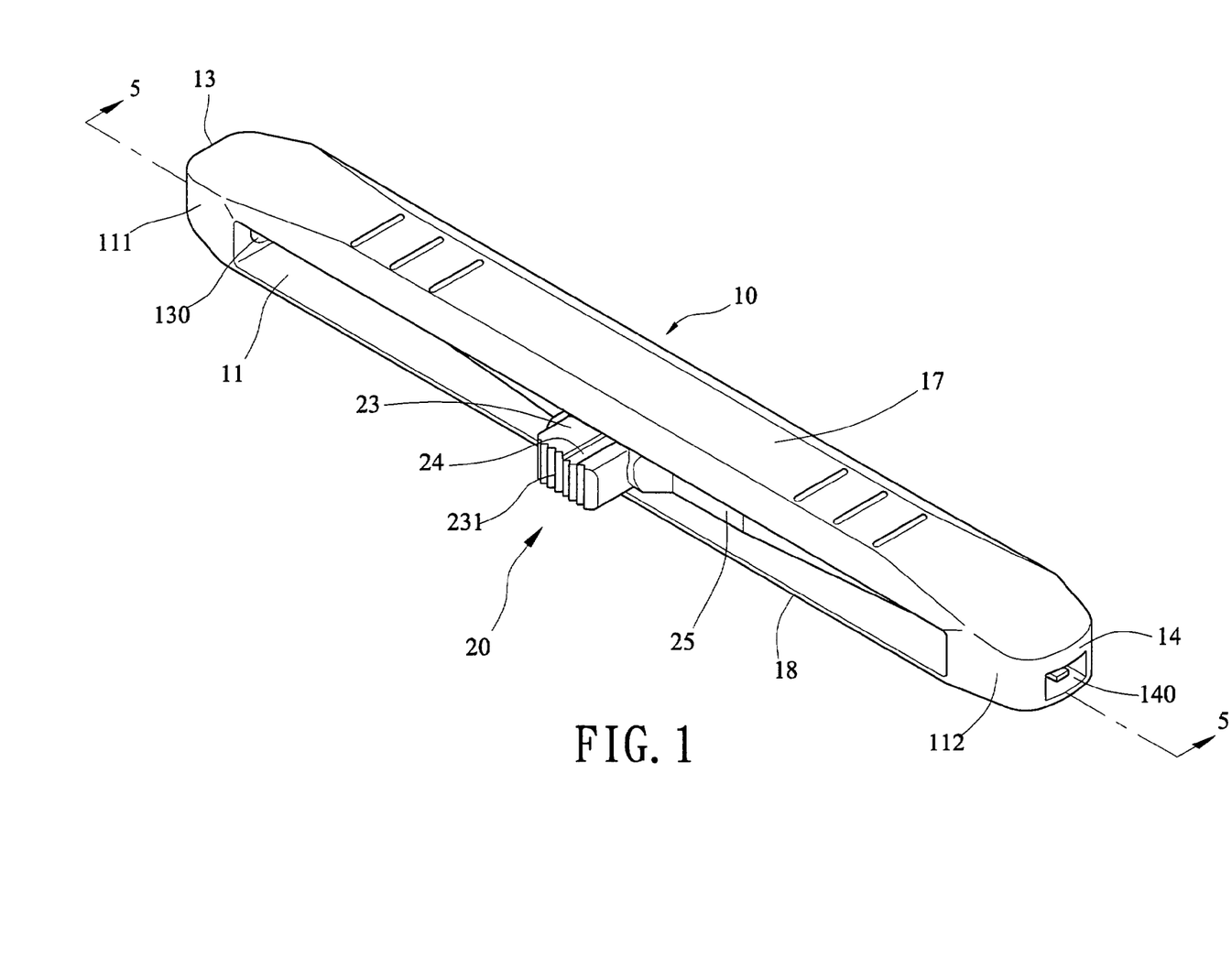
FIG. 1 is a perspective view of a first preferred embodiment of a toothpick and interdental brush combination according to the invention.
Figure 2:
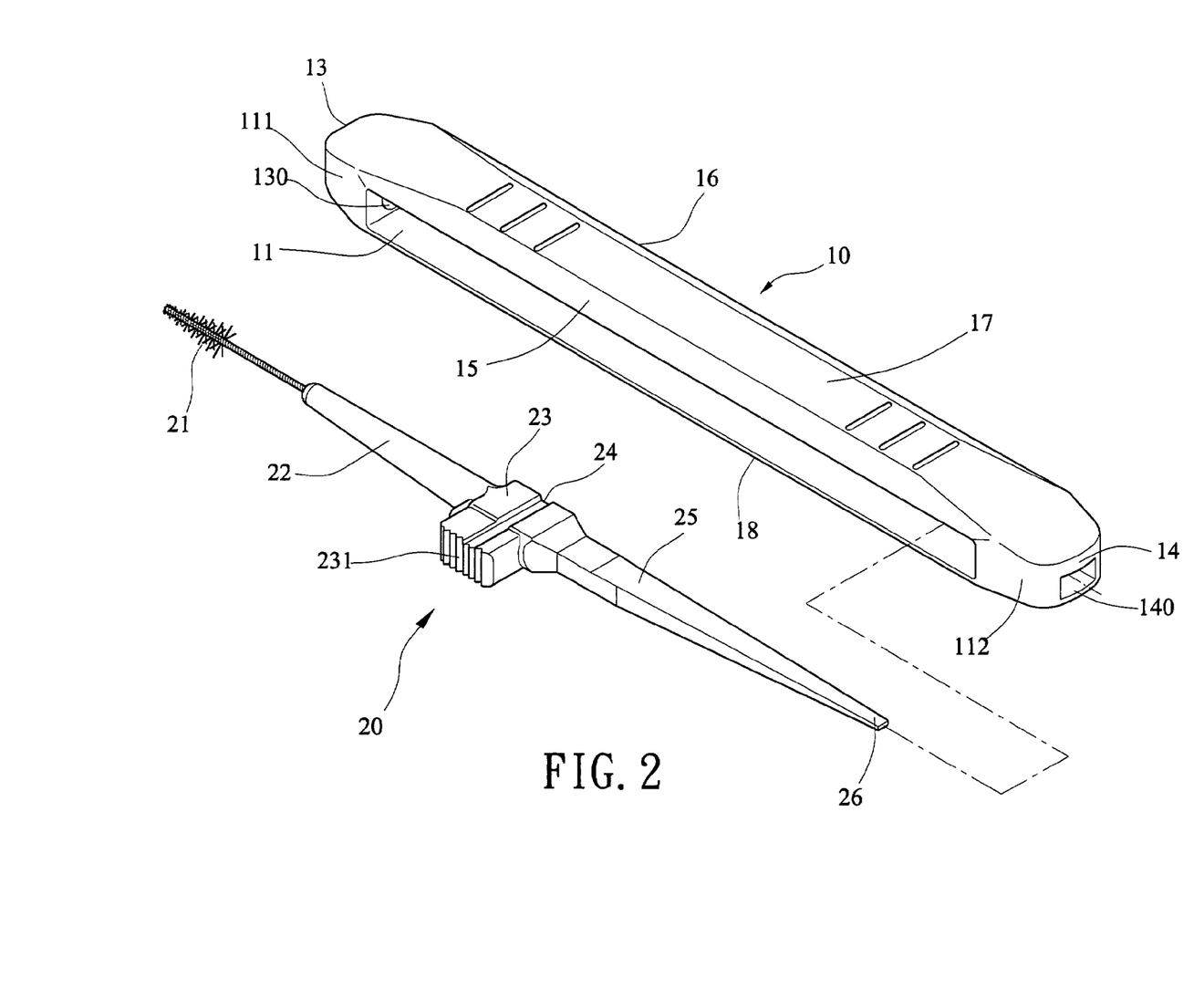
FIG. 2 is an exploded view of FIG. 1.
Figure 3:
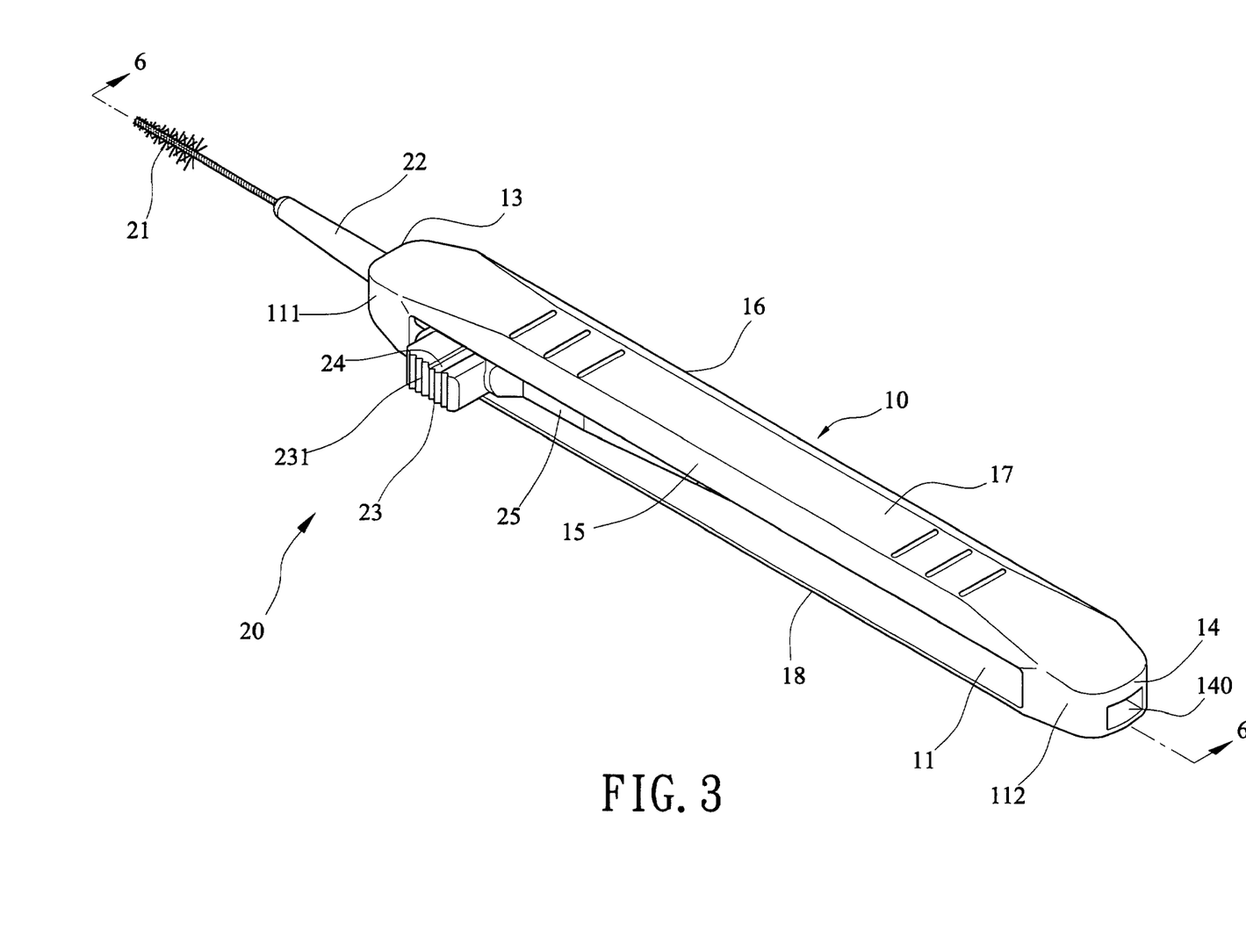
FIG. 3 is a perspective view of the invention with interdental brush pushed to a position for being adapted to use.
Figure 4:
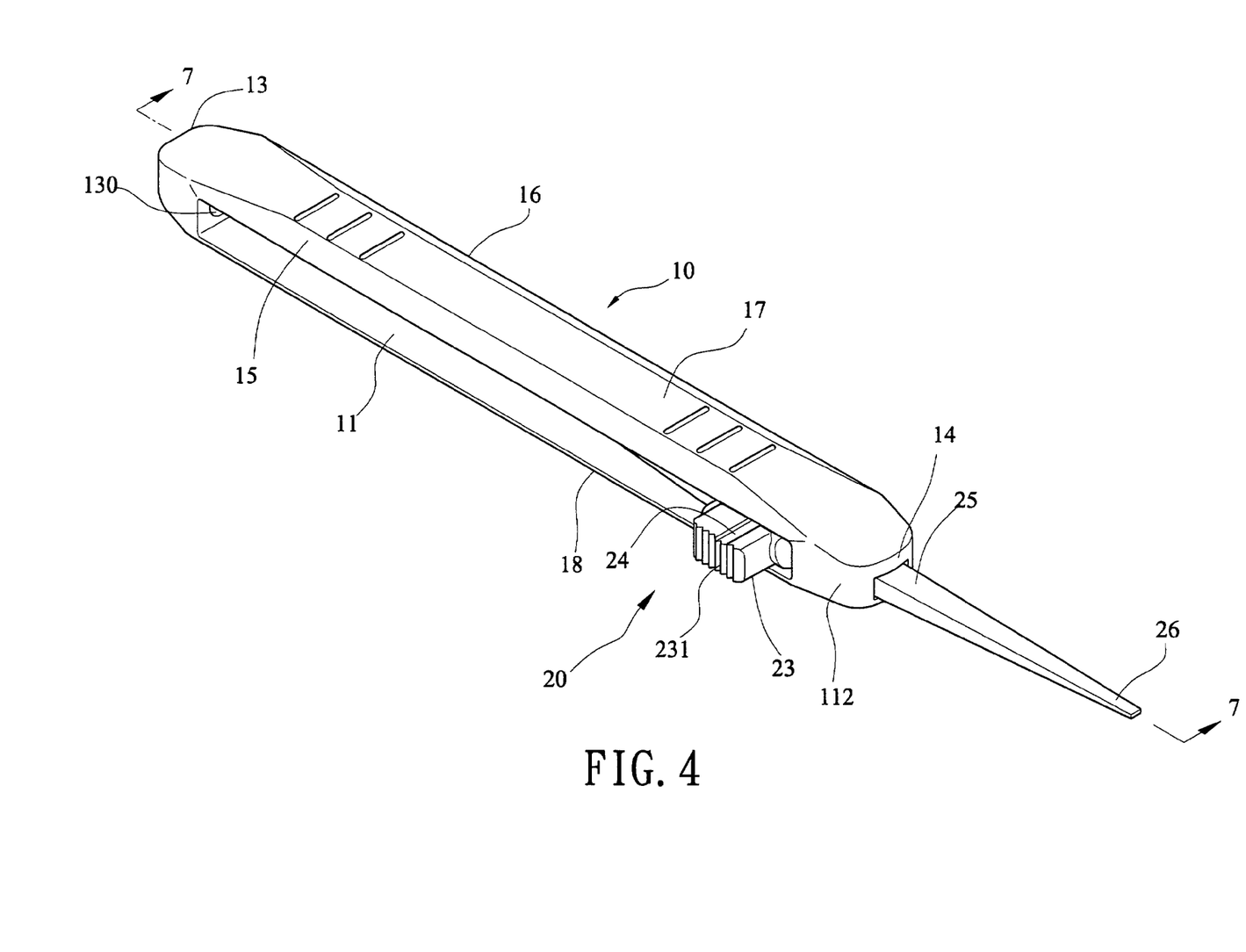
FIG. 4 is another perspective view of the invention with toothpick pushed to a position for being adapted to use.
Figure 5:
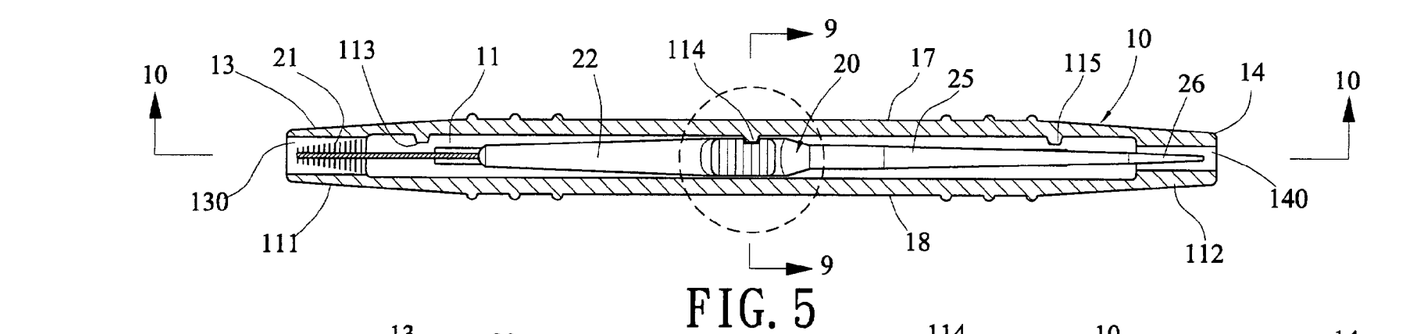
FIG. 5 is a cross-sectional view taken along line 5—5 of FIG. 1.
Figure 6:
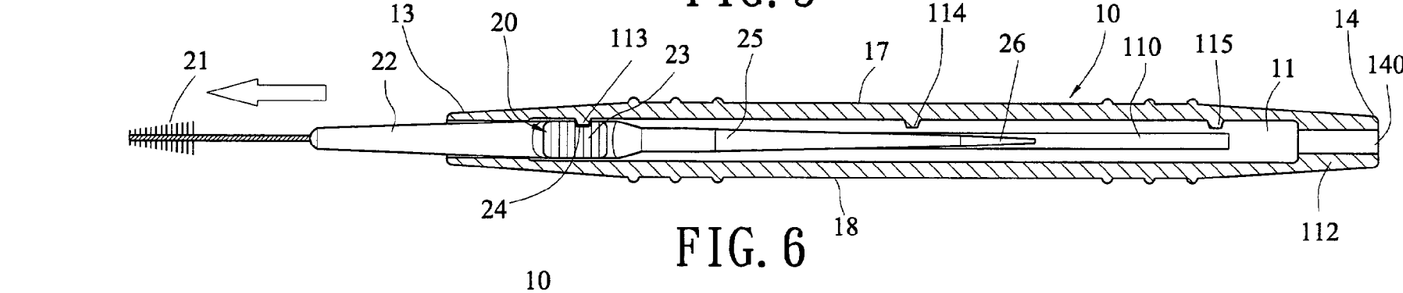
FIG. 6 is a cross-sectional view taken along line 6—6 of FIG. 3.
Figure 7:
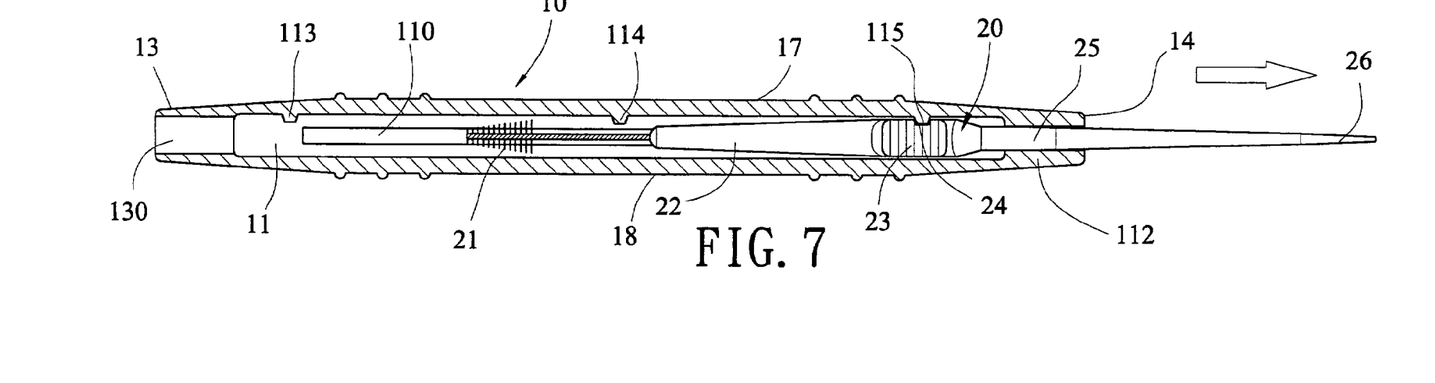
FIG. 7 is a cross-sectional view taken along line 7—7 of FIG. 4.
Figure 8:
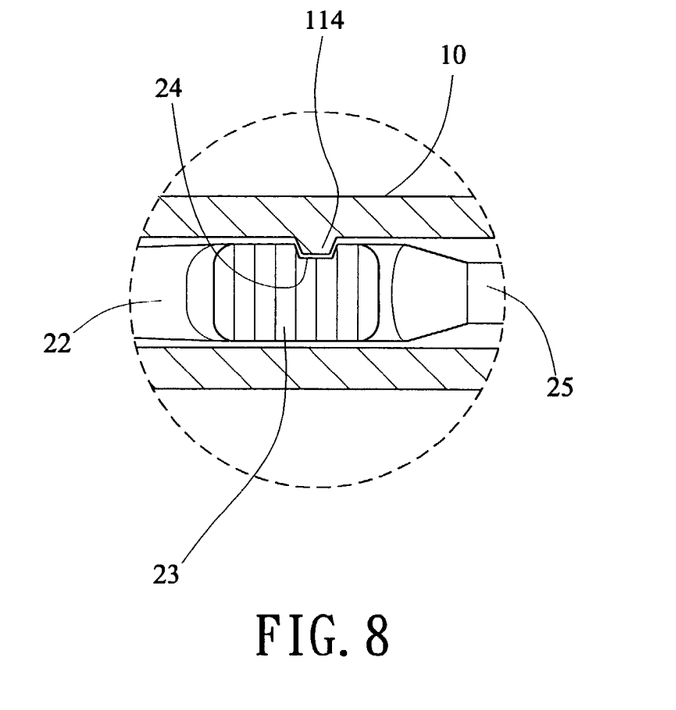
FIG. 8 is a greatly enlarged fragmentary view of a circle shown in FIG. 5.
Figure 9:
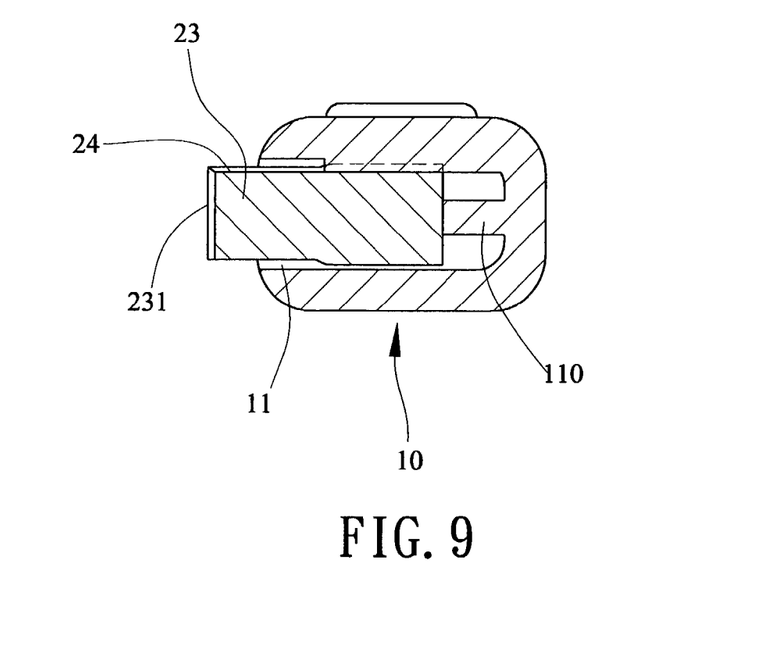
FIG. 9 is a cross-sectional view taken along line 9—9 of FIG. 5.
Figure 10:
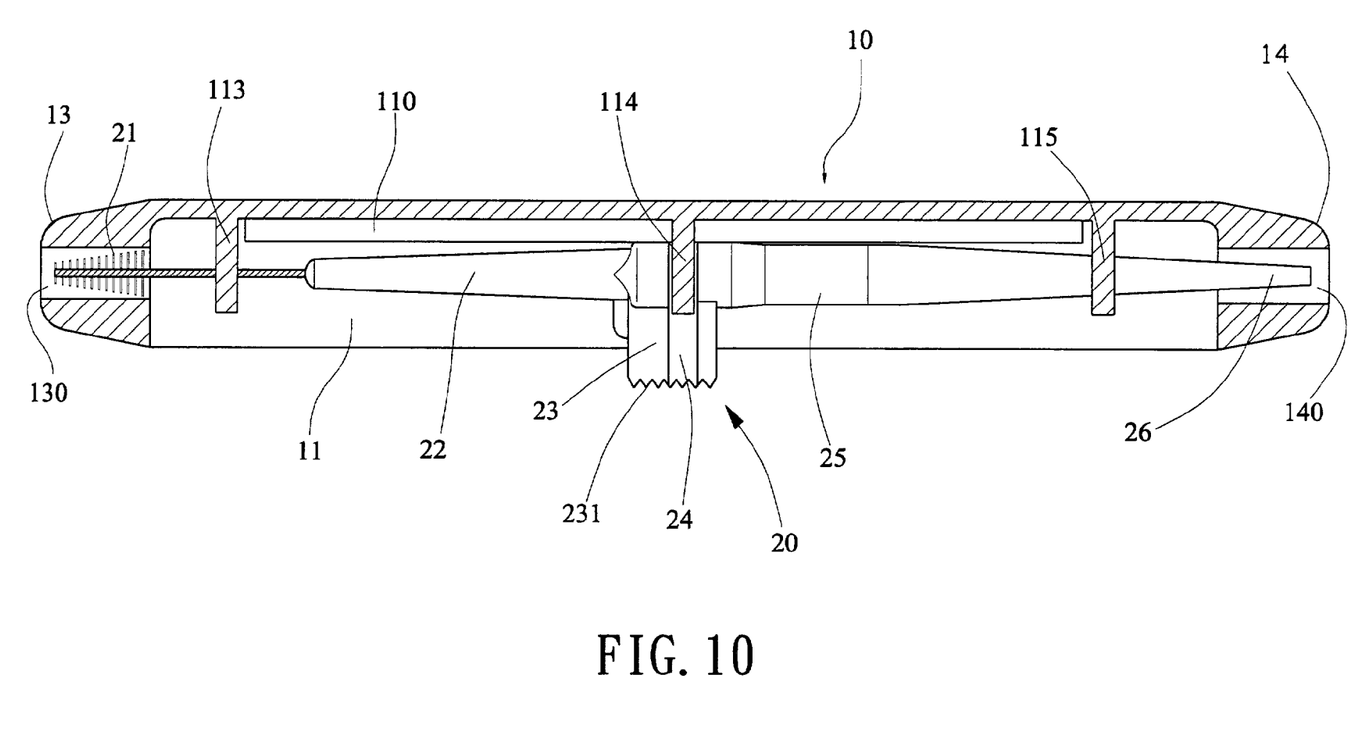
FIG. 10 is a cross-sectional view taken along line 10—10 of FIG. 5.

Referring to FIGS. 1 to 10, there is shown a toothpick and interdental brush combination constructed in accordance with a first preferred embodiment of the invention. The toothpick and interdental brush combination comprises an elongate substantially parallelepiped case 10 and an elongate toothpick and interdental brush assembly 20 slidable in the case 10. Each of above components will now be described in detail below. The case 10 comprises a first end 13, a second end 14, a first side 15, a second side 17, a third side 16, a fourth side 18, a lengthwise groove 11 on the first side 15, an opening 130 at the first end 13, an opening 140 at the second end 14 both in communication with the groove 11, a central ridge 114, a left ridge 113, and a right ridge 115 all on an inner surface of the groove 11 (FIGS. 5 and 10), and a lengthwise central rail 110 on a bottom of the groove 11 (FIG. 9). As seen from FIGS. 5 to 7, a diameter of each of the openings 130 and 140 is slightly smaller than a depth of the groove 11. As shown in FIG. 2, the toothpick and interdental brush assembly 20 comprises a slightly projected central trigger member 23 having a knurled outer surface 231 for ease of pushing by fingers, a central trough 24 on the trigger member 23, a first body member 22 extended from the trigger member 23 toward the left, an interdental brush 21 integrally formed with the first body member 22 at one end, a second body member 25 extended from the trigger member 23 toward the right, and a toothpick 26 integrally formed with the second body member 23 at the other end. Preferably, a width of the trigger member 23 is substantially conformed to that of the groove 11 for ease of mounting therein. Also, a bottom of the trigger member 23 is slidable on the rail 110 for reducing a friction between the trigger member 23 and the groove 11 to a minimum. Thus, the trigger member 23 is slidable in the groove 11 as best shown in FIGS. 5 to 7.

In assembly, first insert the toothpick 26 into the groove 11 to slightly project from the opening 140 until it is possible of placing the whole toothpick and interdental brush assembly 20 in the case 10. Next, push the trigger member 23 toward left until the central ridge 114 is engaged in the trough 24. This completes the assembly (see FIGS. 5, 8, and 10).

In using the interdental brush 21, simply push the trigger member 23 toward left to disengage the central ridge 114 from the trough 24 until the trough 24 is engaged with the left ridge 113. At this position, the interdental brush 21 is completely projected from the opening 130 (FIGS. 3 and 6). Likewise, push the trigger member 23 toward right to disengage the left ridge 113 from the trough 24 until the trough 24 is engaged with the right ridge 115 by passing the central ridge 114. At this position, the toothpick 26 is completely projected from the opening 140 (FIGS. 4 and 7). In view of above, it is found that both the toothpick 26 and the interdental brush 21 are concealed in the case 10 in a storage state while one of them is projected from either opening 130 or 140 in a use state. Thus, it is very convenient in use or storage.

Figure 11:
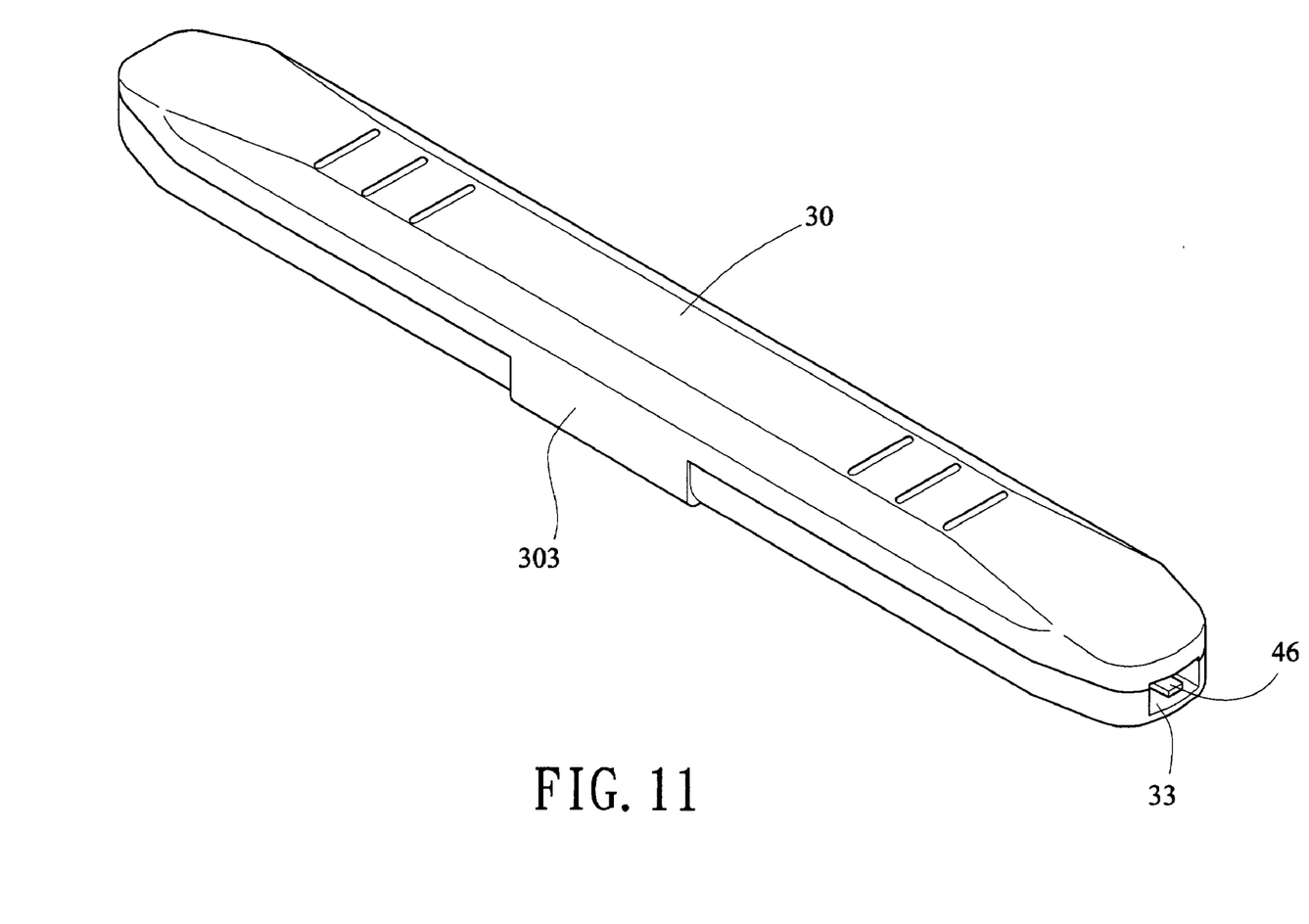
FIG. 11 is a perspective view of a second preferred embodiment of a toothpick and interdental brush combination according to the invention.
Figure 12:
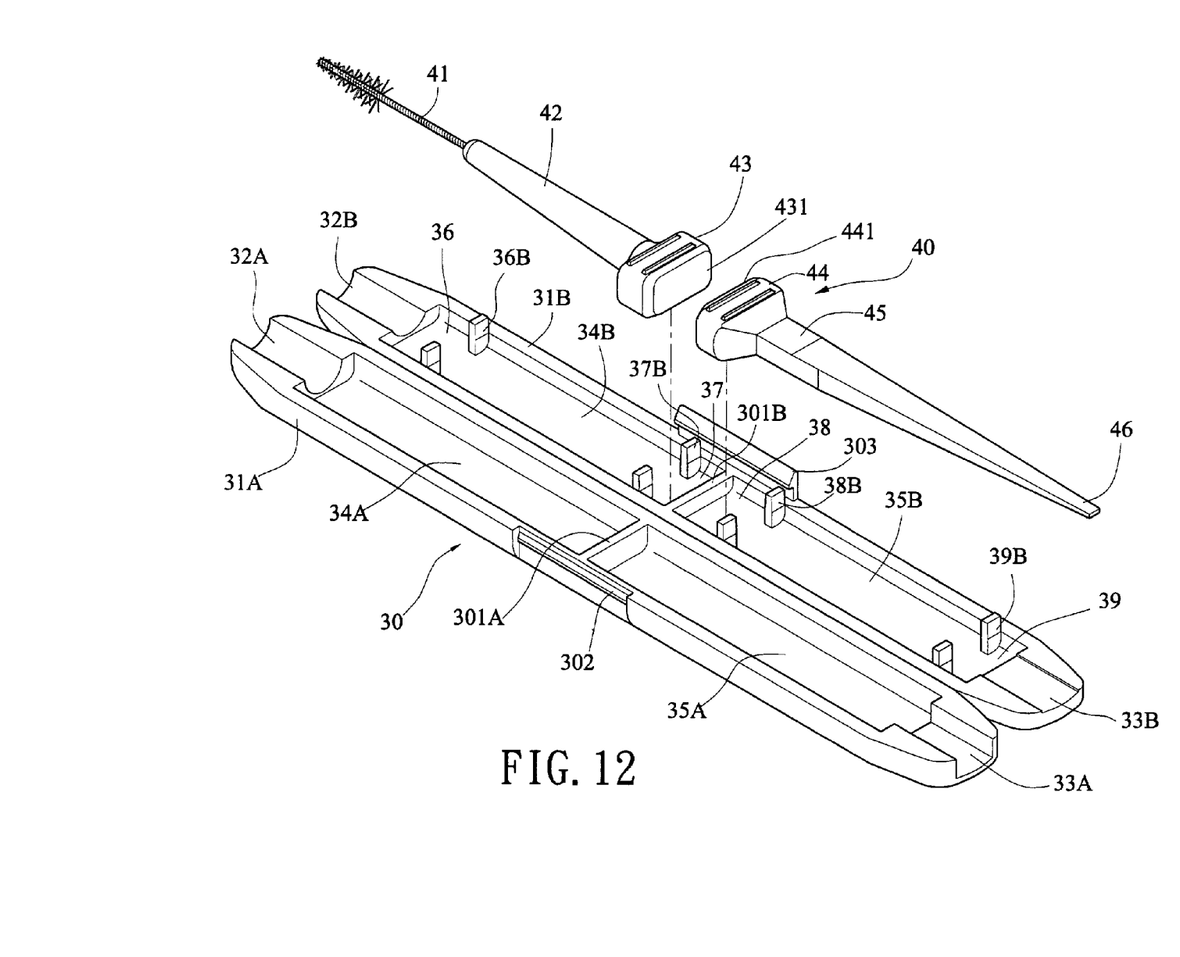
FIG. 12 is an exploded view of FIG. 11.
Figure 13:
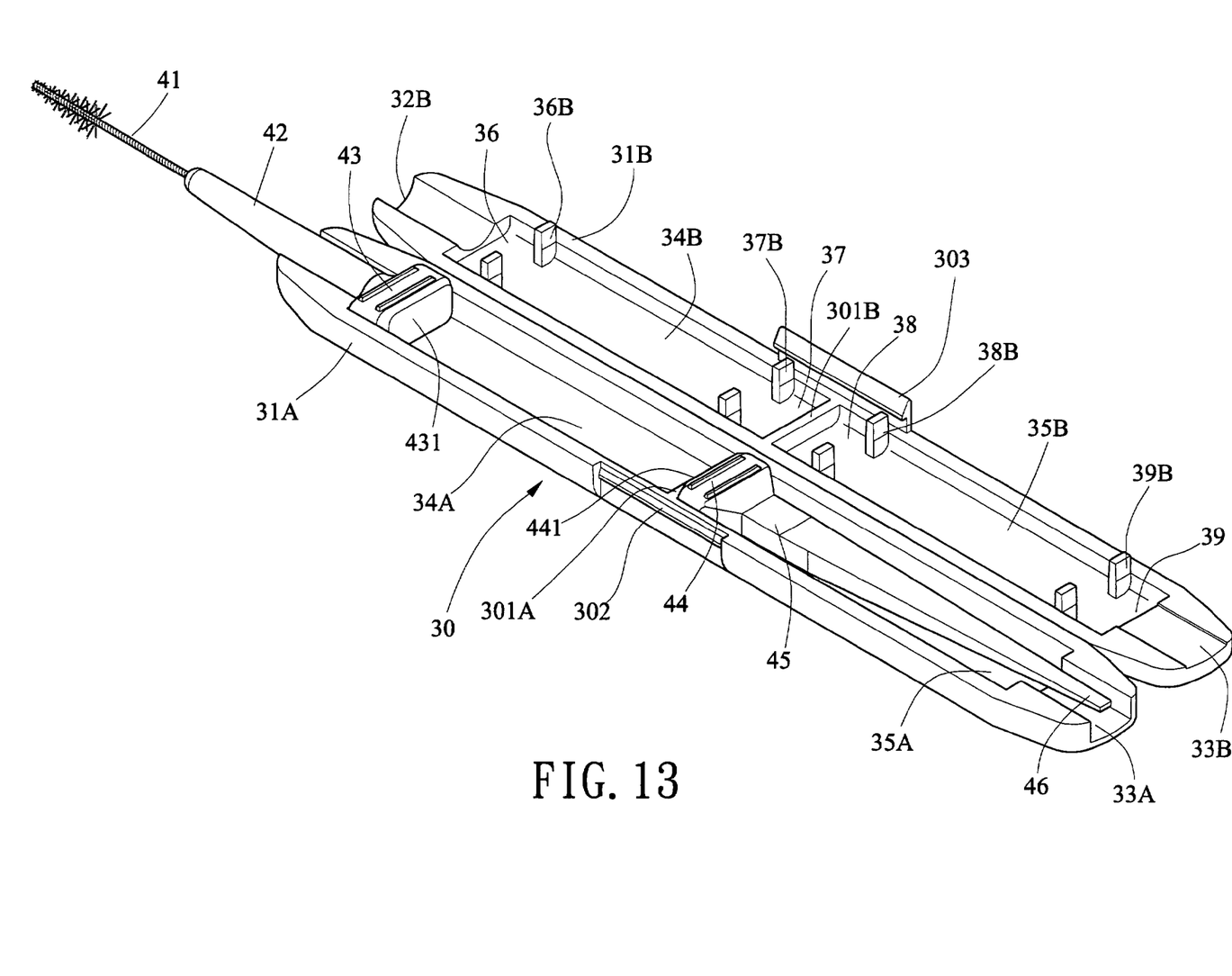
FIG. 13 is a perspective view of the open second preferred embodiment showing interdental brush placed in a use position.

Referring to FIGS. 11 to 16, there is shown a toothpick and interdental brush combination constructed in accordance with a second preferred embodiment of the invention. The characteristics of the second preferred embodiment are detailed below. The toothpick and interdental brush combination comprises an elongate substantially parallelepiped case 30 and a toothpick and interdental brush assembly 40 concealed in the case 30. Each of above components will now be described in detail below. The case 30 comprises a first half case 31A and an integral second half case 31B. The second half case 31B can be pivoted toward the first half case 31A to slide a latch 303 thereof into a slot 302 on the first half case 31A to close the case 30. The case further comprises a first opening 32 at one end consisting of a first half opening 32A and a second half opening 32B for permitting an interdental brush to project therefrom, a second opening 33 at the other end consisting of a third half opening 33A and a fourth half opening 33B for permitting a toothpick to project therefrom, a first compartment 34 consisting of a first half compartment 34A and a second half compartment 34B for receiving the interdental brush, a second compartment 35 consisting of a third half compartment 35A and a fourth half compartment 35B for receiving the toothpick, a central divider 301 consisting of a first half divider 301A and a second half divider 301B for separating the first and the second compartments 34 and 35, two spaced risers 37B on the second half compartment 34B adjacent the second half divider 301 B for forming a first chamber 37, two spaced risers 38B on the fourth half compartment 35B adjacent the second half divider 301 B for forming a second chamber 38, two spaced risers 36B on the second half compartment 34B adjacent the second half opening 32B for forming a third chamber 36, and two spaced risers 39B on the fourth half compartment 35B adjacent the fourth half opening 33B for forming a fourth chamber 39. The toothpick and interdental brush assembly 40 comprises two separate interdental brush and toothpick sections. The interdental brush section comprises an enlargement 43 at one end, the enlargement 43 having an outer flat 431, an interdental brush 41 at the other end, and an intermediate body member 42 integrally formed with the enlargement 43 and the interdental brush 41. Likewise, the toothpick section comprises an enlargement 44 at one end, the enlargement 44 having an outer flat 441, a toothpick 46 at the other end, and an intermediate body member 45 integrally formed with the enlargement 44 and the toothpick 46. In a storage state both the flats 431 and the 441 are abutted the divider 301. Further, the enlargement 43 and 44 are retained in the first and the second chambers 37 and 38 by the risers 37B and 38B respectively. Next, as stated above, a person can close the case 30 by sliding the latch 303 into the slot 302 (FIG. 11).

Figure 14:
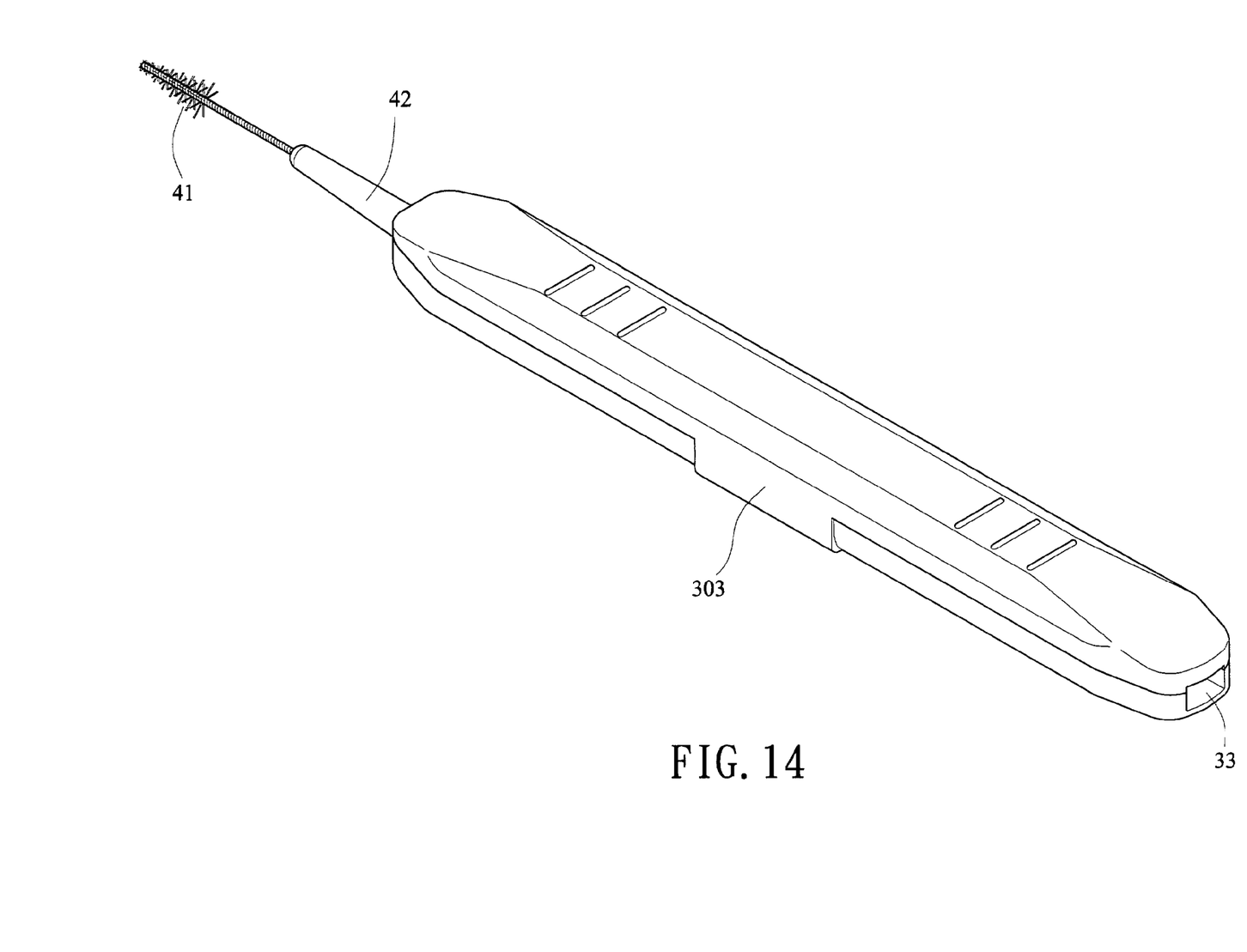
FIG. 14 is a perspective view of the closed second preferred embodiment showing the interdental brush placed in the use position of FIG. 13.
Figure 15:
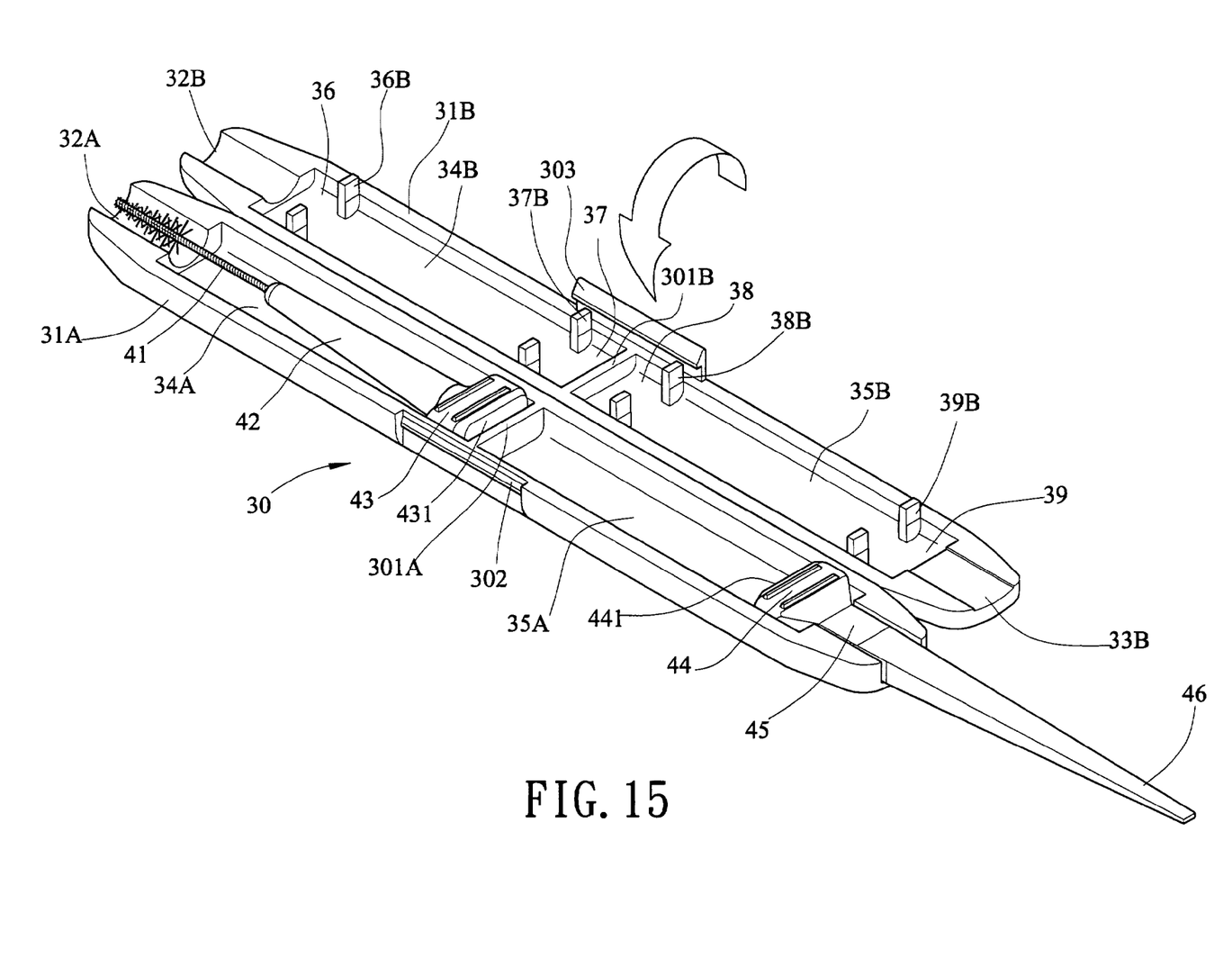
FIG. 15 is a perspective view of the open second preferred embodiment showing toothpick placed in a use position.
Figure 16:
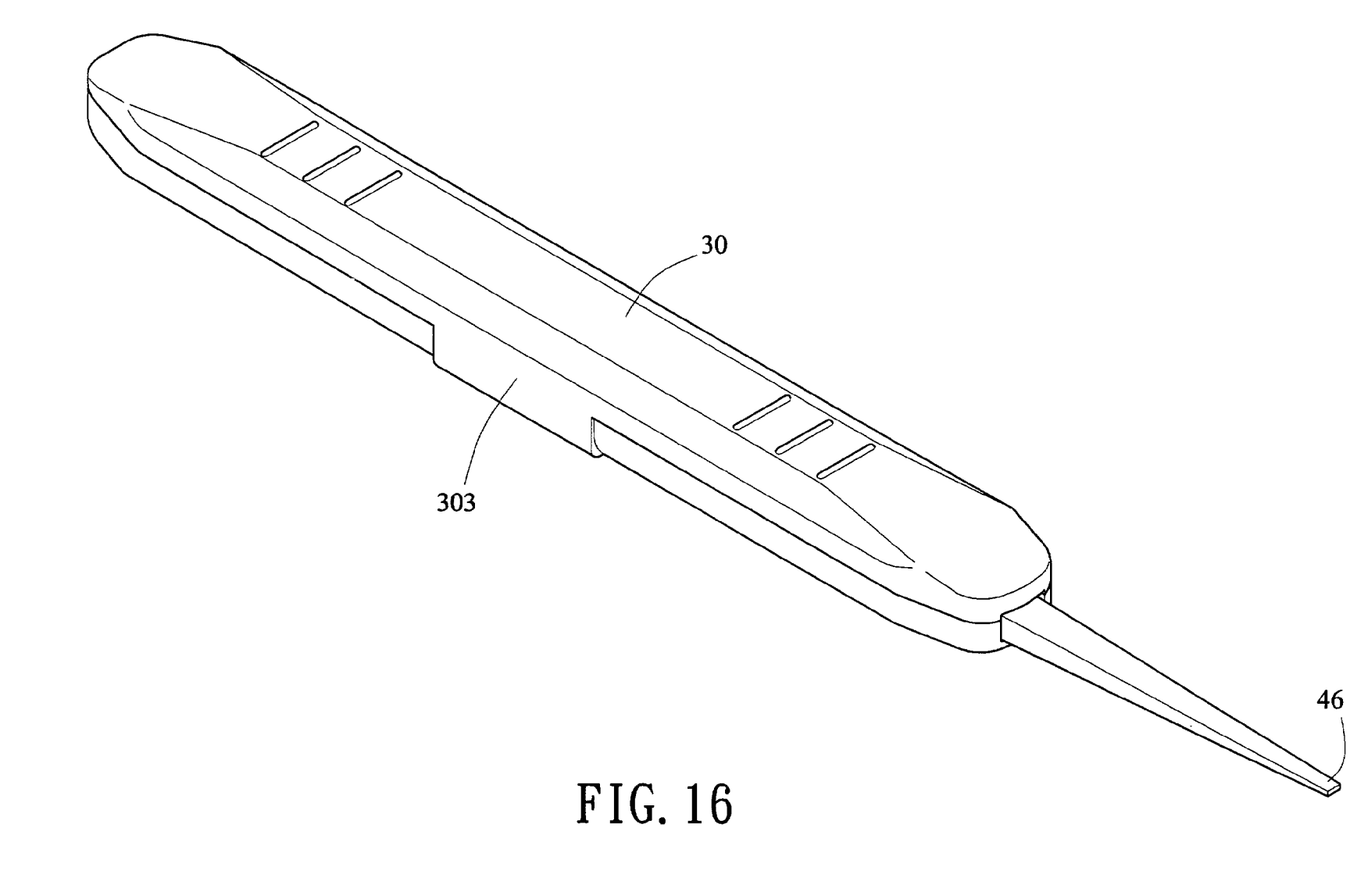
FIG. 16 is a perspective view of the closed second preferred embodiment showing the toothpick placed in the use position of FIG. 15.

In using the interdental brush 41, a person can first open the case 30 by disengaging the latch 303 from the slot 302. Next, move the interdental brush 41 from the position shown in FIG. 12 to that shown in FIG. 13, i.e., the enlargement 43 is located on the third chamber 36 and the interdental brush 41 is projected from the opening 32 and thus retained by the risers 36B. Next, the person can close the case 30 by sliding the latch 303 into the slot 302 (FIG. 14). Likewise, in using the toothpick 46, the person can first open the case 30 by disengaging the latch 303 from the slot 302. Next, move the toothpick 46 from the position shown in FIG. 12 to that shown in FIG. 15, i.e., the enlargement 44 is located on the fourth chamber 39 and the toothpick 46 is projected from the opening 33 and thus retained by the risers 39B. Next, the person can close the case 30 by sliding the latch 303 into the slot 302 (FIG. 16). In view of above, it is found that both the toothpick 46 and the interdental brush 41 are concealed in the case 30 in a storage state while one of them is projected from either opening 32 or 33 in a use state. Thus, it is very convenient in use or storage.

Figure 17:
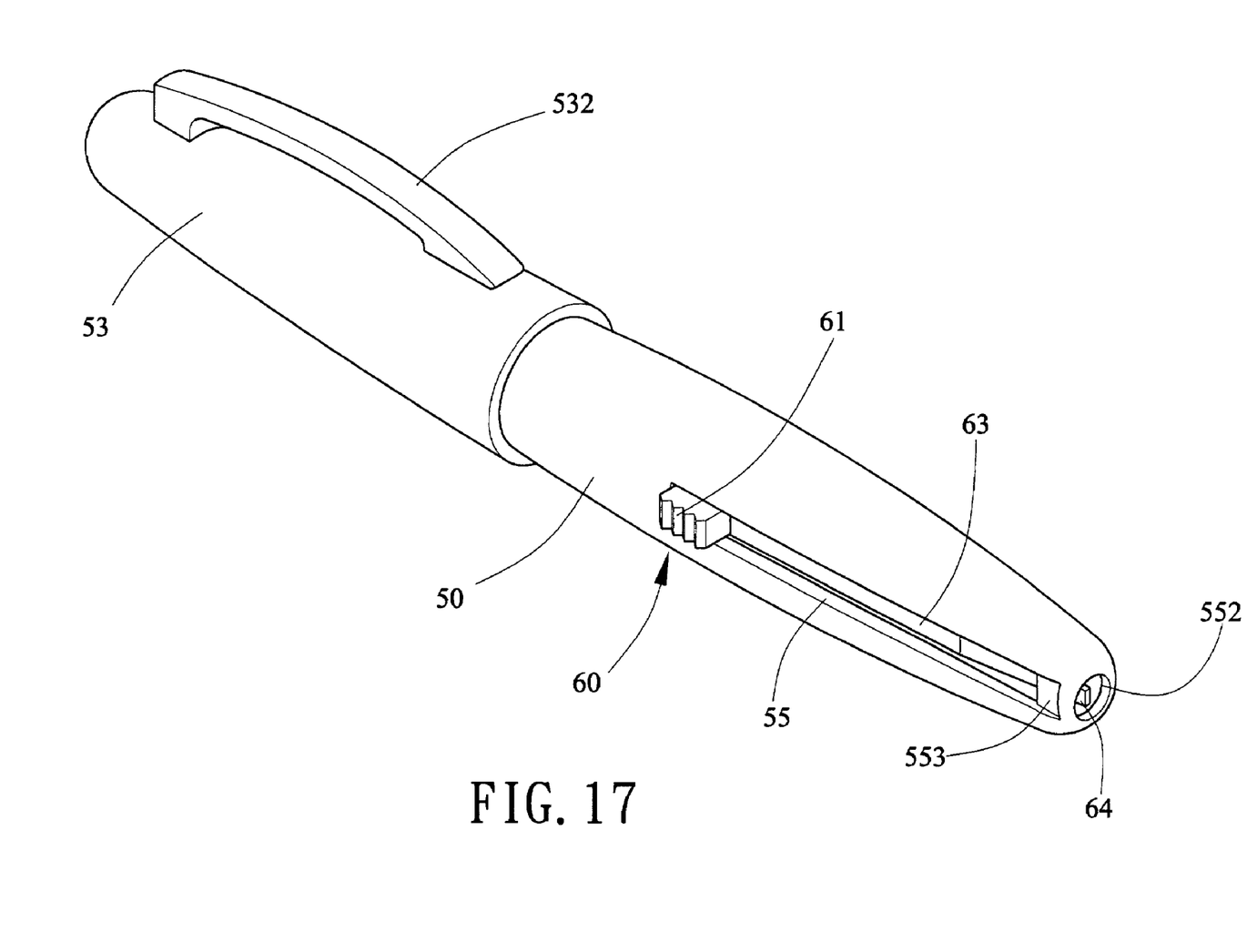
FIG. 17 is a perspective view of a third preferred embodiment of a toothpick and interdental brush combination according to the invention.
Figure 18:
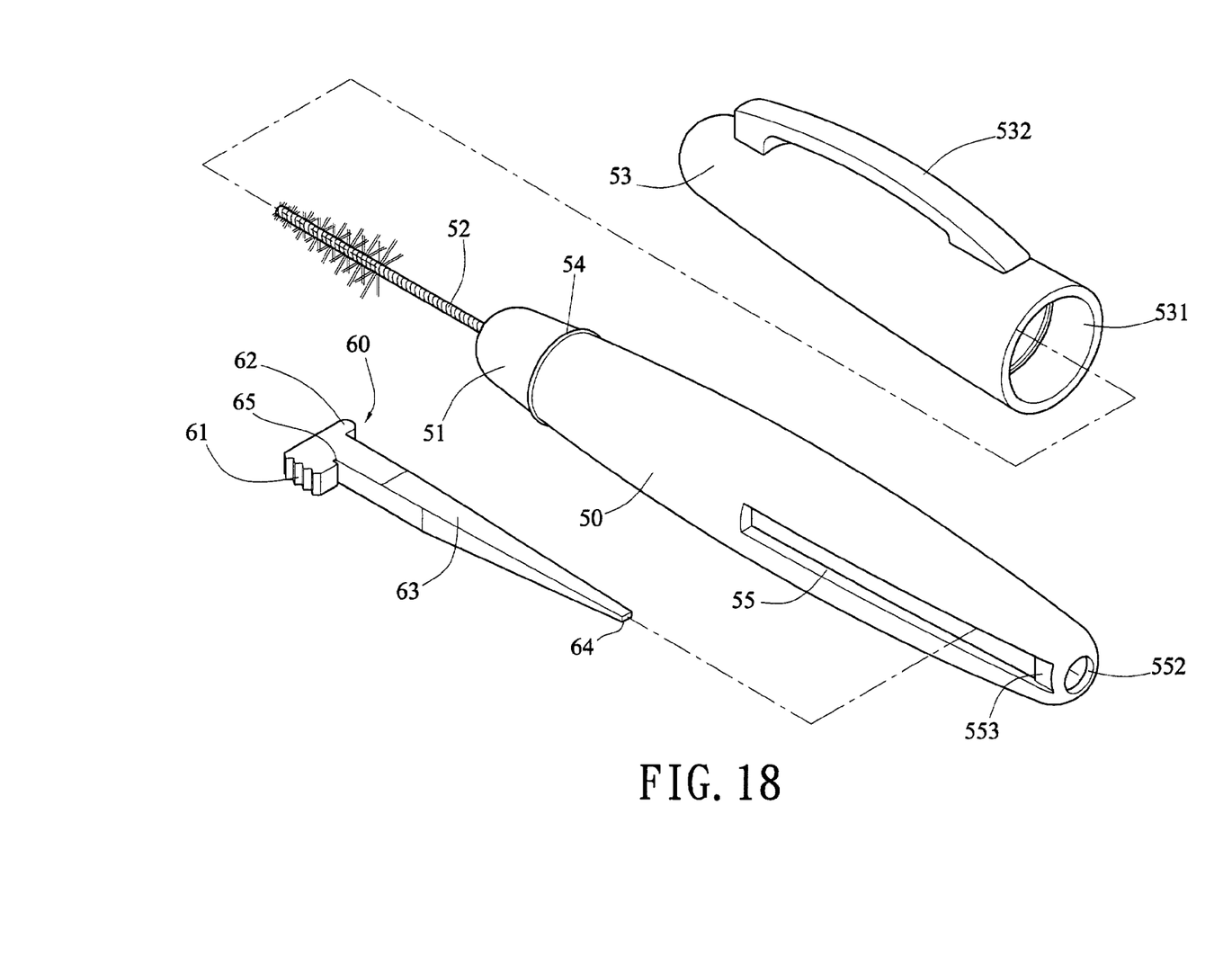
FIG. 18 is an exploded view of FIG. 17.
Figure 19:
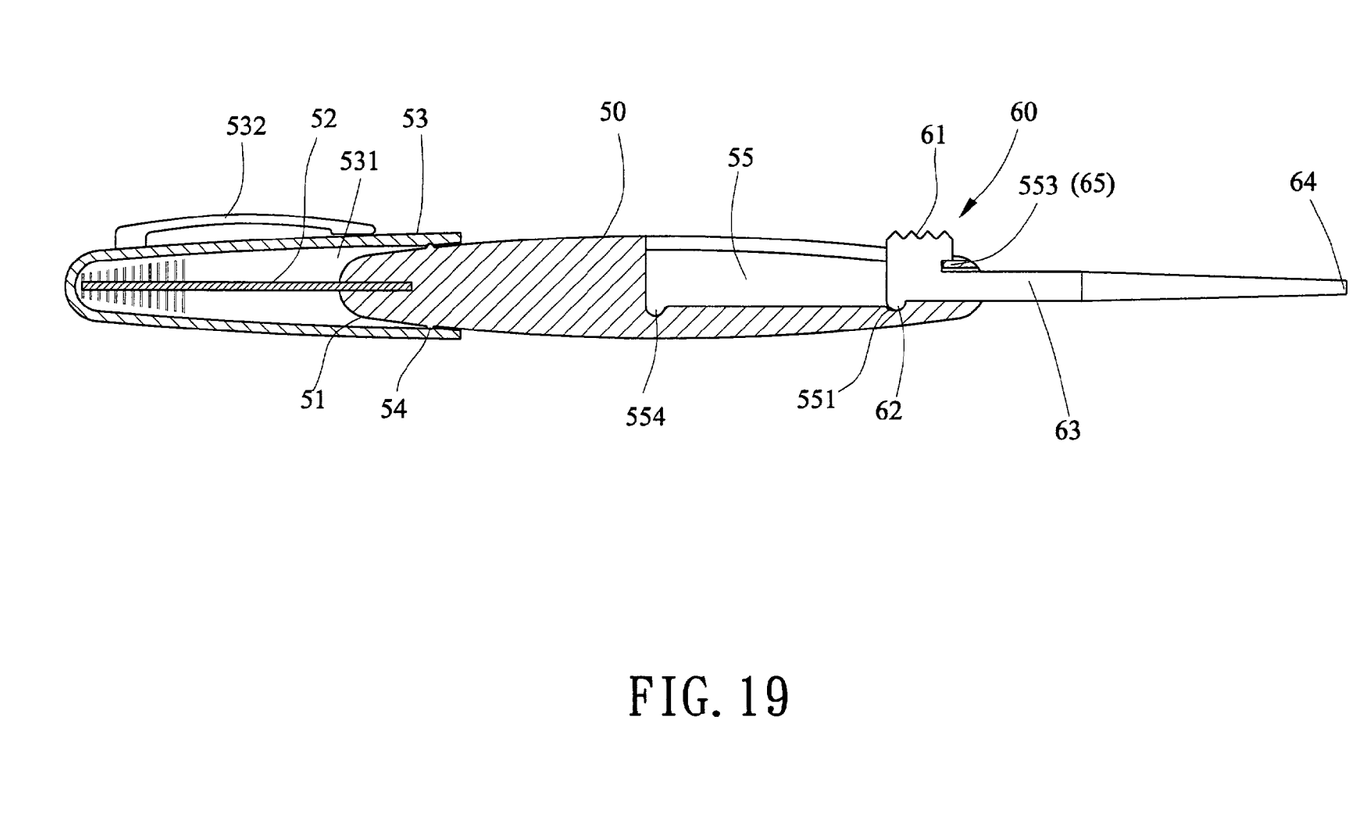
FIG. 19 is a cross-sectional view of the third preferred embodiment with toothpick pushed to a position for being adapted to use.

Referring to FIGS. 17 to 19, there is shown a toothpick and interdental brush combination constructed in accordance with a third preferred embodiment of the invention. The characteristics of the third preferred embodiment are detailed below. The toothpick and interdental brush combination is shaped as a fountain pen and comprises a cap 53 and an oval toothpick and interdental brush assembly 50. Each of above components will now be described in detail below. The toothpick and interdental brush assembly 50 comprises a first end 51, an interdental brush 52 extended from the first end 51, a separate toothpick mechanism 60 at the other end, the toothpick mechanism 60 comprising a knurled section 61 at one end for ease of pushing by fingers, a projection 62 opposite to the knurled section 61, a toothpick 64 at the other end, and a body member 63 integrally formed with the toothpick 64, the knurled section 61, and the projection 62, a recess 65 between the knurled section 61 and the body member 63, an elongate groove 55 for permitting the toothpick mechanism 60 to slide therein, an opening 552 at the other second end for permitting the toothpick 64 to extend therethrough or retract therefrom, a first indentation 551 on a bottom of the groove 55 proximate the opening 552, a second indentation 554 also on the bottom of the groove 55 distal from the opening 552, a latch 553 at the other end of the groove 55 insertable into the recess 65, and a collar 54 proximate the first end 51. The cap 53 comprises a clip 532 for fastening to a foreign object in a storage state and an opening 531 having an internal annular recess for securing to the toothpick and interdental brush assembly 50 by engaging with the collar 54 by snapping. In a storage state, the cap 53 is put on the toothpick and interdental brush assembly 50 with the collar 54 engaged in the internal annular recess of the opening 531 and the toothpick mechanism 60 is slid to abut one end of the groove 55 for concealing the toothpick 64 in the toothpick and interdental brush assembly 50 with the projection 62 engaged in the second indentation 554 for fastening.

In using the interdental brush, simply remove the cap 53 from the toothpick and interdental brush assembly 50. In using the toothpick, first put the cap 53 on the toothpick and interdental brush assembly 50 if they are disengaged. Next, slide the toothpick mechanism 60 by pushing the knurled section 61 toward the other end of the groove 55 (i.e., the projection 62 is moved from the position of the second indentation 554 toward that of the first indentation 551) until, as stated above, the latch 553 is inserted into the recess 65 and the projection 62 is engaged in the first indentation 551 for fastening. At this position, the toothpick 64 is completely projected from the opening 552. In view of above, it is found that both the toothpick 64 and the interdental brush 52 are concealed in the toothpick and interdental brush assembly 50 in a storage state while one of them is projected in a use state. Thus, it is very convenient in use or storage. In addition to advantages of portability and being ease of storage and use, the invention is hygienic.

While the invention herein disclosed has been described by means of specific embodiments, numerous modifications and variations could be made thereto by those skilled in the art without departing from the scope and spirit of the invention set forth in the claims.

What is claimed is:

1. A toothpick and interdental brush combination comprising:
   a) an elongated substantially parallelepiped case having:
      i) a first opening located on a first end thereof;
      ii) a second opening located on a second end thereof;
      iii) a lengthwise groove located in a first side thereof and communicating with the first and the second openings; and
      iv) a central ridge, a first ridge, and a second ridge located in the lengthwise groove;
   b) an elongated toothpick and interdental brush assembly slidably located in the lengthwise groove and having:
      i) a trigger member located in a middle thereof and having a central trough selectively engaging one of the central ridge, the first ridge, and the second ridge;
      ii) an interdental brush located on a first end thereof and movable between a retracted and extended brush positions, in the retracted brush position, the interdental brush being located within the lengthwise groove, in the extended brush position, the interdental brush protruding outwardly from the first opening; and
      iii) a toothpick located on a second end thereof and movable between a retracted and extended toothpick positions, in the retracted toothpick position, the toothpick being located within the lengthwise groove, in the extended toothpick position, the toothpick protruding outwardly from the second opening, the trigger assembly being located between the interdental brush and the toothpick,
   wherein, the trigger member controlling movements of the interdental brush and the toothpick, when the interdental brush is in the retracted brush position and the toothpick is in the retracted toothpick position the central trough engaging the central ridge, when the interdental brush is in the extended brush position and the toothpick is in the retracted toothpick position the central trough engaging the first ridge, and when the interdental brush is in the retracted brush position and the toothpick is in the extended toothpick position the central trough engaging the second ridge.

2. The toothpick and interdental brush combination according to claim 1, wherein the elongated substantially parallelepiped case includes a lengthwise central rail located on a bottom of the lengthwise groove, a bottom of the trigger member being slidable on the lengthwise central rail.

3. The toothpick and interdental brush combination according to claim 1, wherein the elongated toothpick and interdental brush assembly includes a first body member located between the trigger member and the interdental brush, and a second body member located between the trigger member and the toothpick.

* * * * *